United States Patent
Sever et al.

(10) Patent No.: US 10,379,020 B2
(45) Date of Patent: Aug. 13, 2019

(54) VIBRATION FATIGUE TESTING

(71) Applicant: ROLLS-ROYCE plc, London (GB)

(72) Inventors: Ibrahim A Sever, Derby (GB); Dario Di Maio, Bristol (GB); Fabrizio Magi, Bristol (GB)

(73) Assignee: ROLLS-ROYCE PLC, London (GB)

( * ) Notice: Subject to any disclaimer, the term of this patent is extended or adjusted under 35 U.S.C. 154(b) by 429 days.

(21) Appl. No.: 15/156,831

(22) Filed: May 17, 2016

(65) Prior Publication Data
US 2016/0363518 A1 Dec. 15, 2016

(30) Foreign Application Priority Data

Jun. 15, 2015 (GB) .................................. 1510408.6

(51) Int. Cl.
*G01N 3/32* (2006.01)
*G01M 7/02* (2006.01)
(Continued)

(52) U.S. Cl.
CPC ............ *G01N 3/32* (2013.01); *G01M 5/0033* (2013.01); *G01M 5/0066* (2013.01);
(Continued)

(58) Field of Classification Search
CPC ........ G01N 3/32; G01N 29/045; G01N 29/11; G01N 29/14; G01N 29/44;
(Continued)

(56) References Cited

U.S. PATENT DOCUMENTS 2,625,659 A * 1/1953 Mendelson .............. G01N 3/38
250/231.1
2,779,190 A * 1/1957 Benda ...................... G01N 3/32
73/577
(Continued)

FOREIGN PATENT DOCUMENTS

CN 104748928 A 7/2015
GB 2 367 631 A 4/2002
(Continued)

OTHER PUBLICATIONS

Dec. 7, 2015 Search Report issued in Great Britain Patent Application No. GB1510408.6.
(Continued)

*Primary Examiner* — Lisa M Caputo
*Assistant Examiner* — Rose M Miller
(74) *Attorney, Agent, or Firm* — Oliff PLC

(57) ABSTRACT

A method to determine a fatigue limit for a material. Form a test component including the material. Identify a resonant frequency of the component and an excitation frequency which causes the component to vibrate. Measure a response parameter of the component when excited at the excitation frequency. Test the component to determine its fatigue limit by sub-steps to: apply an excitation force to the component at the excitation frequency to cause vibration of the component; alter the applied excitation force at constant excitation frequency to maintain the response parameter constant; measure at least one of an input parameter and an output parameter; iterate the sub-steps to alter and measure until the first order, second order, or first and second order derivatives of the input parameter and/or output parameter exhibit a discontinuity. Repeat the steps for a different excitation frequency. The fatigue limit for the material includes all the identified discontinuities.

10 Claims, 4 Drawing Sheets

(51) Int. Cl.
*G01M 5/00* (2006.01)
*G01N 29/44* (2006.01)
*G01N 29/04* (2006.01)
*G01N 29/11* (2006.01)
*G01N 29/14* (2006.01)
*G01N 33/00* (2006.01)

(52) U.S. Cl.
CPC ............ *G01M 7/022* (2013.01); *G01M 7/025* (2013.01); *G01N 29/045* (2013.01); *G01N 29/11* (2013.01); *G01N 29/14* (2013.01); *G01N 29/44* (2013.01); *G01N 2033/0003* (2013.01); *G01N 2203/0073* (2013.01); *G01N 2203/0218* (2013.01); *G01N 2203/0244* (2013.01); *G01N 2203/0688* (2013.01); *G01N 2291/028* (2013.01); *G01N 2291/0231* (2013.01); *G01N 2291/0258* (2013.01)

(58) Field of Classification Search
CPC ... G01N 2033/0003; G01N 2203/0073; G01N 2203/0218; G01N 2203/0244; G01N 2203/0688; G01N 2291/0231; G01N 2291/0258; G01N 2291/028; G01M 5/0033; G01M 5/0066; G01M 7/022; G01M 7/025
USPC ................................. 73/577, 862.41, 862.59
See application file for complete search history.

(56) References Cited

U.S. PATENT DOCUMENTS

| | | | | |
|---|---|---|---|---|
| 2,788,659 | A * | 4/1957 | Radnar | G01N 3/38 331/156 |
| 3,027,757 | A * | 4/1962 | Achter | G01N 3/38 73/571 |
| 3,374,662 | A * | 3/1968 | Achter | G01N 3/32 73/571 |
| 7,953,561 | B2 | 5/2011 | Musial et al. | |
| 8,621,934 | B2 | 1/2014 | Hughes et al. | |
| 2009/0048788 | A1 | 2/2009 | Darehbidi et al. | |
| 2013/0261987 | A1 | 10/2013 | Grant et al. | |
| 2014/0067285 | A1 | 3/2014 | Khonsari et al. | |

FOREIGN PATENT DOCUMENTS

| | | |
|---|---|---|
| JP | S62-71829 A | 4/1987 |
| WO | 93/22651 A1 | 11/1993 |
| WO | 2010/102208 A1 | 9/2010 |

OTHER PUBLICATIONS

Lazan, B. et al., "Dynamic Testing of Materials and Structures With a New Resonance-Vibration Exciter and Controller." WADC Technical Report 52-252, pp. 1-42, (1952).

Claeys, J. et al., "Characterisation of a Resonant Bending Fatigue Test Setup for Pipes." Laboratory Soet, Sustainable Construction and Design, pp. 424-431 (2011).

Kuznetsov, N. D. et al., "Pneumatic Excitation of High-Frequency Resonance Vibrations of Elements Made of Composite Materials." Problemy Prochnosti, No. 4, pp. 59-63 (1990).

Kee et al., "Resonant Fatigue Testing of Full-Scale Composite Helicopter Rotor Blades." (2012), pp. 1-4.

Gu, Jun et al., "The Study of Resonance Fatigue Testing of Test Beams Made of Composite Material." (2009).

Cesnik, M. et al., "Uninterrupted and Accelerated Vibrational Fatigue Testing With Simultaneous Monitoring of the Natural Frequency and Damping.", Journal of Sound and Vibration, vol. 331, pp. 5370-5382, (2012).

Bertini, L. et al., "Resonant Bench for Fatigue Testing of Steel Drill Pipe Connections."

Tafti, Mohamad Ahmadi, "Experimental High Cycle Fatigue Testing and Shape Optimization of Turbine Blades.", pp. 1-93, (2013).

White, D. et al., "Evaluation of the New B-Rex Fatigue Testing System for Multi-Megawatt Wind Turbine Blades.", presented at 43rd AIAA Aerospace Sciences Meeting and Exhibit, pp. 1-14, (2004).

Abdullah, A.B.M, "Development of a Closed-Loop Resonant Fatigue Testing Methodology and Experimental Life Test of Aluminum Alloy.", pp. 1-120, (2010).

Lazan, B.J., "Fatigue Failure Under Resonant Vibration Conditions.", Wright Air Development Center, pp. 1-49, (1954).

Nov. 9, 2016 Search Report issued in European Patent Application No. 16169831.

* cited by examiner

VIBRATION FATIGUE TESTING

The present disclosure concerns a method of testing materials. In particular it concerns a method to determine a vibration fatigue limit of a material, for example a composite material.

Known methods to determine a vibration fatigue limit of a material relate to metals. A test component is vibrated at its resonant frequency. Structural degradation of metals is generally linked to critical events in which serious rupture of the material occurs. The fatigue limit is defined by the stress or strain versus number of cycles after which critical events are expected to occur.

Composite materials are formed of layers of resin, which may include aligned, woven or chopped fibres. Structural degradation of composite materials is therefore less abrupt than in metals, for example comprising micro-cracking. If left unchecked, micro-cracks can join up and eventually cause delamination. Micro-cracking causes a reduction in the stiffness of the composite material without a critical event causing a step change in stiffness. Known methods of determining a vibration fatigue limit, developed for metals, are therefore less effective for composite materials.

It is therefore desirable to find a method to determine a vibration fatigue limit of a material.

According to a first aspect of the invention there is provided a method to determine a fatigue limit for a material comprising steps to:
  form a test component comprising the material;
  identify a resonant frequency of the test component;
  identify an excitation frequency which causes the test component to vibrate;
  measure a response parameter of the test component when excited at the excitation frequency;
  test the test component to determine its fatigue limit by sub-steps to:
    apply an excitation force to the test component at the excitation frequency to cause vibration of the test component;
    alter the applied excitation force at constant excitation frequency to maintain the response parameter constant;
    measure at least one of an input parameter and an output parameter;
    iterate the steps to alter and measure until the first order derivative, second order derivative, or first and second order derivatives of the input parameter and/or first order derivative, second order derivative, or first and second order derivatives of the output parameter exhibit a discontinuity;
  repeat the steps for a different excitation frequency; and
  define the fatigue limit for the material to include all the identified discontinuities.

Advantageously the method is suitable for determining a vibration fatigue limit. In particular, it is suitable for determining the vibration fatigue limits of materials which do not exhibit abrupt failure but instead experience gradual degradation. The method can be used to determine the vibration fatigue limit of composite materials. It can also be used to determine the vibration fatigue limit of metals or ceramics.

Advantageously the method may be applied via standard vibration fatigue test equipment. Particularly there may be an actuator to excite vibration of the test component at the excitation frequency and one or more sensor to measure the input parameters, output parameters and response parameters.

The input parameter may comprise one or more of excitation force, acceleration, velocity, displacement, voltage and current. The input power may be determined therefrom.

The output parameter may comprise one or more of response phase, acceleration, velocity, displacement, voltage and current.

The first order derivative may be determined by plotting the input parameter and/or output parameter against number of vibration cycles and identifying a point where the gradient of the plotted line changes. The second order derivative may be determined by plotting the input parameter and/or output parameter against number of vibration cycles and identifying a point where the rate of change of gradient of the plotted line changes. The first order derivative and second order derivative may each be determined by plotting. Advantageously the first order derivative and/or the second order derivative exhibits a discontinuity, for example an elbow. The discontinuity corresponds to the fatigue limit of the material to that force and excitation frequency combination.

The step of plotting may comprise plotting logarithmically.

The step of testing may comprise a high cycle fatigue test. This may comprise $10^5$ to $10^7$ cycles in a test.

The response parameter of the test component may comprise amplitude of vibration, stress or strain.

The step of repeating may comprise repeating for a different resonant frequency. Advantageously it is possible to test the material's reaction to frequency by targeting each resonant frequency individually using the method. A discontinuity, elbow, of the first order derivative and/or a second order derivative may be identified for each test.

The method may comprise a further step to determine a failure limit of the material. The further step may comprise applying a multiplier to the fatigue limit. Advantageously the difference between the failure limit and the fatigue limit may indicate the remaining useful life of a component made from the material.

The material may comprise a composite material.

The skilled person will appreciate that except where mutually exclusive, a feature described in relation to any one of the above aspects may be applied mutatis mutandis to any other aspect. Furthermore except where mutually exclusive any feature described herein may be applied to any aspect and/or combined with any other feature described herein.

Embodiments will now be described by way of example only, with reference to the Figures, in which.

Figure 1:
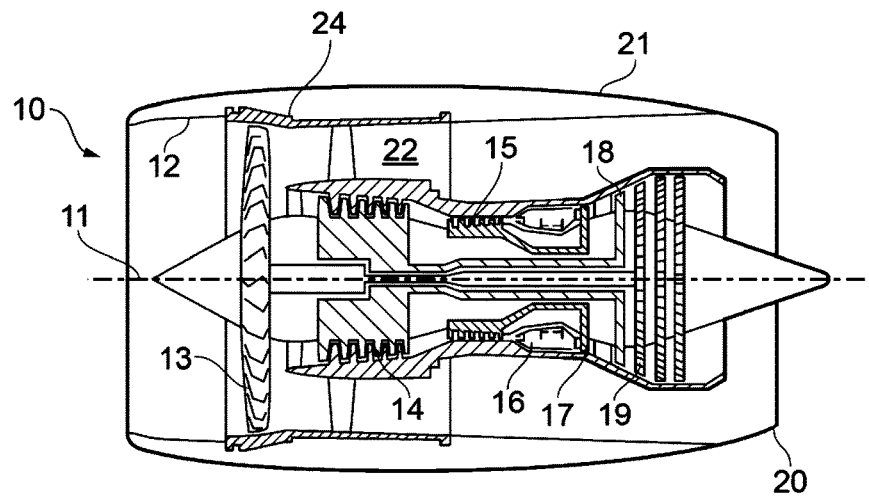
FIG. 1 is a sectional side view of a gas turbine engine.

With reference to FIG. 1, a gas turbine engine is generally indicated at 10, having a principal and rotational axis 11. The engine 10 comprises, in axial flow series, an air intake 12, a propulsive fan 13, an intermediate pressure compressor 14, a high-pressure compressor 15, combustion equipment 16, a high-pressure turbine 17, and intermediate pressure turbine 18, a low-pressure turbine 19 and an exhaust nozzle 20. A nacelle 21 generally surrounds the engine 10 and defines both the intake 12 and the exhaust nozzle 20.

The gas turbine engine 10 works in the conventional manner so that air entering the intake 12 is accelerated by the fan 13 to produce two air flows: a first air flow into the intermediate pressure compressor 14 and a second air flow which passes through a bypass duct 22 to provide propulsive thrust. The intermediate pressure compressor 14 compresses the air flow directed into it before delivering that air to the high pressure compressor 15 where further compression takes place.

The compressed air exhausted from the high-pressure compressor 15 is directed into the combustion equipment 16 where it is mixed with fuel and the mixture combusted. The resultant hot combustion products then expand through, and thereby drive the high, intermediate and low-pressure turbines 17, 18, 19 before being exhausted through the nozzle 20 to provide additional propulsive thrust. The high 17, intermediate 18 and low 19 pressure turbines drive respectively the high pressure compressor 15, intermediate pressure compressor 14 and fan 13, each by suitable interconnecting shaft.

Other gas turbine engines to which the present disclosure may be applied may have alternative configurations. By way of example such engines may have an alternative number of interconnecting shafts (e.g. two) and/or an alternative number of compressors and/or turbines. Further the engine may comprise a gearbox provided in the drive train from a turbine to a compressor and/or fan.

Gas turbine engine components such as fan blades, the engine casing, integral rafts for pipes and/or cabling on the exterior of the engine, fuel tanks, pipes, and other externals may be formed of composite material. Such composite material may include a metal matrix, aligned fibres, chopped fibres or woven fibres. These components and others may alternatively be formed of metals, ceramics or other materials.

Material fatigue may be defined as the weakening of a material caused by repeatedly applied loads. Cyclical loading causes progressive and localised structural degradation of a component. The stress which causes such fatigue is typically lower than the strength of the material, indicated by yield strength or tensile strength, but accumulates over repeated application. A fatigue limit is a theoretical value below which the material is not expected to fail due to cyclical loading.

For high cycle fatigue of a component an S-N curve can be determined. High cycle fatigue is typically defined as between $10^5$ and $10^7$ cycles, whilst very high cycle fatigue is typically defined as over $10^7$ cycles. For completeness, low cycle fatigue is generally defined as between $10^4$ and $10^5$ cycles. The S-N curve plots cyclic stress (in MPa) against number of cycles to failure (usually plotted on a logarithmic scale), which indicates the material's life. Generally the higher the cyclic stress the shorter the material life to failure. The S-N curve is typically determined through testing of samples of the material with the number of cycles to failure being an average which indicates the probable material life for a given cyclic stress.

Figure 2:
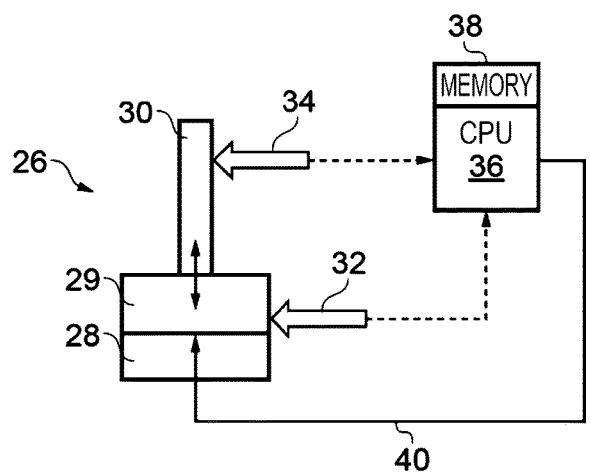
FIG. 2 is a schematic illustration of high cycle vibration test equipment.

FIG. 2 illustrates vibration test equipment 26. The equipment 26 includes a support 28 which is arranged to support a test component 30. The support 28 includes an exciter or actuator 29 to vibrate the test component 30 at a predetermined excitation frequency $f_e$. The vibration is illustrated by a double-headed arrow. One or more input probe 32 is arranged to measure an input parameter of the test. For example the input probe 32 may measure the excitation frequency $f_e$. It may also or alternatively measure any one or more of the force F, acceleration a or velocity v of excitation.

One or more output probe 34 is arranged to measure an output parameter of the test. For example the output probe 34 may measure one or more of the vibration amplitude A, the resonant frequency $f_r$ of the test component 30, or the phase $\phi$ of the vibration. One or more than one of the output parameters may be measured by an output probe 34. Each input probe 32 and output probe 34 may measure one or more of the parameters.

There may be more than one input probe 32 and/or more than one output probe 34. Measurements from multiple input probes 32 may be averaged or otherwise combined for redundancy and robustness of measurement. Similarly, measurements from multiple output probes 34 may be averaged or otherwise combined for redundancy and robustness of measurement. There may be one or more input probes 32 measuring each input parameter. There may be one or more output probes 34 measuring each output parameter.

The vibration test equipment 26 may also include a processor 36. The processor 36 is arranged to receive the measurements from the input probe or probes 32 and from the output probe or probes 34, as shown by the dashed arrows. The processor 36 processes the measurements, as will be described, to determine the fatigue limit of the test component 30. The processor 36 further includes or is coupled to memory 38 in which it stores the fatigue limit of the test component 30 and pertinent information about the test component 30. The processor 36 determines the fatigue limit of the material from which the test component 30 is formed from the accumulated fatigue limits of similar test components 30 which are subjected to various vibration tests within the equipment 26.

The processor 36 may also generate control signals 40 which are passed to the exciter or actuator 29. The control signals 40 may define the excitation force F and excitation frequency $f_e$ to be applied to the test component 30. The processor 36 may be arranged to calculate the excitation force F and/or excitation frequency $f_e$ on the basis of the measurements received from the input probe 32 and/or output probe 34. Alternatively the processor 36 may access predetermined test programmes that are stored in the memory 38 and which define the excitation force F and excitation frequency $f_e$.

A method of testing a test component 30 formed of a composite material is now described. The method uses the equipment 26 shown in FIG. 2. First, a resonant frequency $f_r$ of the test component 30 is identified. The test component 30 may have more than one resonant frequency $f_r$, in which case one of the resonant frequencies $f_r$ is chosen. There is no set criterion by which one of the resonant frequencies $f_r$ should be chosen. A resonant frequency $f_r$ is a natural vibration frequency of the test component 30 which is governed by the material properties. It is identified by a local maximum in the amplitude measurement.

Second, an excitation frequency $f_e$ is identified which causes the test component 30 to vibrate. The excitation frequency $f_e$ may be the same frequency as the resonant frequency $f_r$ or may be a different frequency which acts as a forcing frequency.

Third, the amplitude of vibration A of the test component 30 is measured when excited at the excitation frequency $f_e$. This amplitude A is a local maximum where the excitation frequency $f_e$ is the same as the resonant frequency $f_r$. The amplitude A associated with a different resonant frequency $f_r$ may be larger. The amplitude A is not a local maximum where the excitation frequency $f_e$ is not coincident with (the same as) the resonant frequency $f_r$.

Fourth, the test component 30 is tested to determine its fatigue limit by a series of sub-steps. In a first sub-step an excitation force F is applied to the test component 30, via the exciter or actuator 29, at the excitation frequency $f_e$. This causes the test component 30 to vibrate at the determined amplitude of vibration A.

In a second sub-step the excitation force F is increased whilst the excitation frequency $f_e$ is maintained at a constant frequency. The excitation force F is increased at a rate which maintains the amplitude of vibration A constant. The excitation force F has to be increased in order to achieve this because as micro-cracks form in the test component 30 its stiffness changes (reduces) and so its resonant frequency $f_r$ shifts from that initially measured. By maintaining the excitation frequency $f_e$ at a constant value more energy must be applied through the forcing (excitation force F) in order to maintain the amplitude A of the vibration at its initial value.

In a third sub-step of the method the excitation force F or the response phase φ of the test component 30 is measured. The response phase φ is the difference between an excitation (input) parameter and the equivalent response (output) parameter. For example the parameter may be velocity v, acceleration a or displacement. The excitation force F may be measured directly. Alternatively the acceleration a and/or velocity v of the applied vibration may be measured by observing the displacement of the actuator 29. The input power P can be calculated from the excitation force F and velocity v, or from the mass m, acceleration a and velocity v, or from the voltage and current input to the actuator 29, or in any other known way. As the excitation force F is increased to maintain the constant vibration amplitude A, the acceleration a also increases. The response phase φ is a measure of the movement of the resonant frequency $f_r$ away from its initial value as the test component 30 degrades.

The second sub-step may alternatively comprise decreasing the excitation force F whilst the excitation frequency $f_e$ is maintained at constant frequency. This is the case where the excitation frequency $f_e$ is set below the resonant frequency $f_r$. The excitation force F is decreased at a rate which maintains the amplitude of vibration A constant as the resonant frequency $f_r$ shifts from that initially measured. Consequently the acceleration a also decreases.

The second and third sub-steps are iterated. The iteration continues until it is possible to determine the fatigue limit of the test component 30. In practice it is usually necessary to increase the excitation force F beyond the fatigue limit of the test component 30 in order to determine that limit. The limit is determined as a discontinuity of the first order derivative and/or the second order derivative of the input power P, one of its constituents such as the excitation force F or acceleration a, or the response phase φ.

Figure 3:
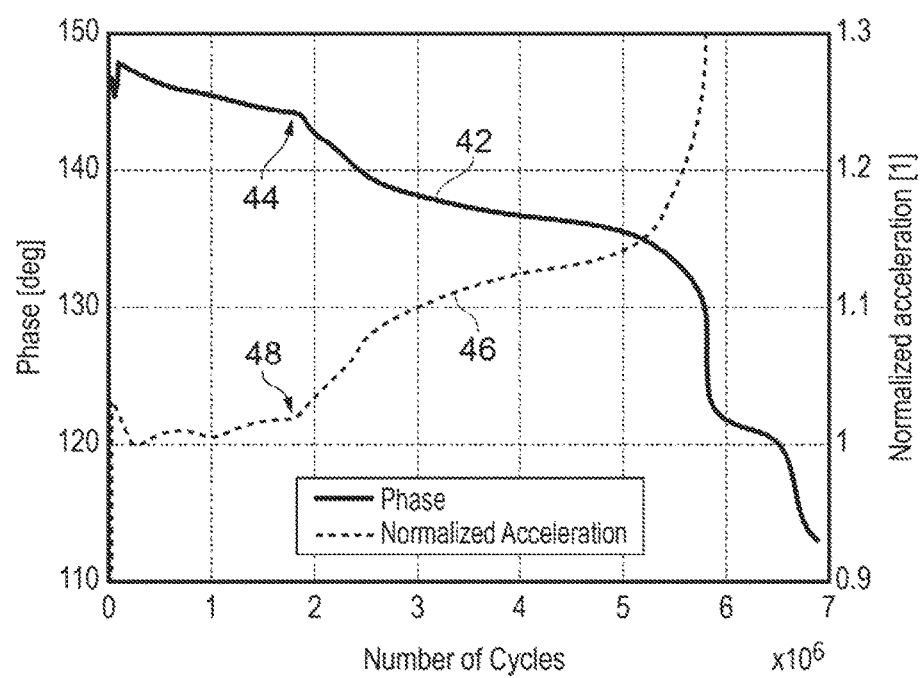
FIG. 3 is a graph showing response phase and normalised acceleration each plotted against number of cycles.

FIG. 3 is an exemplary plot of measurements taken in the third sub-step in multiple iterations. The response phase φ is shown by line 42. An elbow 44 can be seen in the line 42 at approximately $1.8 \times 10^6$ cycles. At the elbow 44 the gradient of the line 42 changes abruptly. Thus the rate of change of the gradient is discontinuous at the elbow 44. The rate of change of the gradient of the line 42 is, mathematically, the second order derivative of the response phase φ and the elbow 44 is the point of discontinuity.

Similarly line 46 shows the normalised acceleration a. An elbow 48 can be seen in the line 46, which also occurs at approximately $1.8 \times 10^6$ cycles. At the elbow 48 the gradient of the line 46 changes abruptly; the rate of change of the gradient is thus discontinuous at the elbow 48. Mathematically the rate of change of the gradient of line 48 is the second order derivative of the acceleration a.

The elbow 44 on line 42 and the elbow 48 on line 46 occur at the same number of cycles because one is a measure of an input parameter and the other is a measure of an output parameter. However, both the input and output parameters are affected by the same increase in structural degradation, such as the accumulation of micro-cracking. Thus both the input and output parameters reach a critical accumulation of structural damage at the same number of cycles resulting in the elbows 44, 48 of the gradients.

The fatigue limit of the test component 30 is therefore ascertained from the elbow 44, 48 of the gradient of the response phase φ and/or acceleration a. The steps of the method can be repeated, using different but equivalent test components 30. Particularly, when the steps are repeated a different excitation frequency $f_e$ may be chosen at which to force the test component 30 to resonate. A different resonant frequency $f_r$ may also be chosen with the excitation frequency $f_e$ chosen to force the test component 30 to resonate at or near the resonant frequency $f_r$. The steps of the method can be repeated with a different excitation force F applied in the first sub-step.

Figure 4:
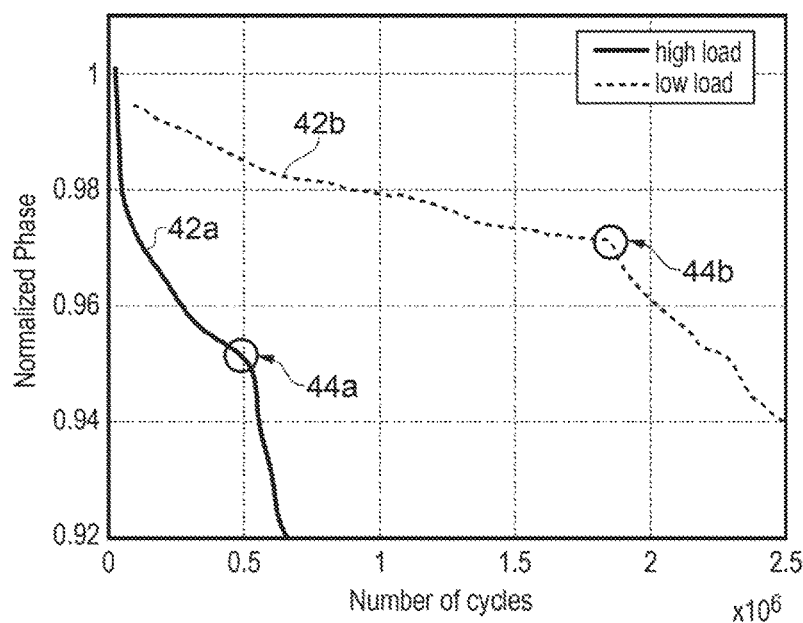
FIG. 4 is a graph showing normalised phase plotted against number of cycles.

FIG. 4 shows two lines 42a, 42b of the response phase φ, normalised to 1 at zero cycles where there is no movement from the initial phase, each line 42a, 42b relating to a different vibration test of an equivalent test component 30. One line 42a corresponds to a high load; the other line 42b corresponds to a lower load. As is apparent the phase φ changes more quickly in response to the high load, line 42a, than in response to the lower load, line 42b. Thus the gradient of the high load line 42a is much steeper than the lower load line 42b. Each line 42a, 42b exhibits an elbow 44a, 44b at which the gradient (first order derivative) and/or the rate of change of the gradient (second order derivative) of the line 42a, 42b is discontinuous.

Figure 5:
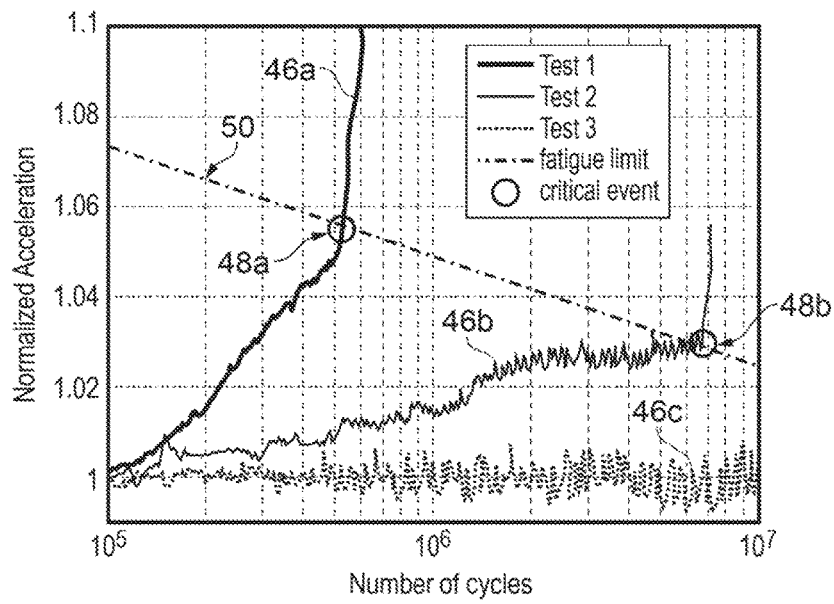
FIG. 5 is a graph showing normalised acceleration plotted against number of cycles and fatigue limit.

The fatigue limit 50 of the composite material can be generated by plotting a line through the elbows 44, 48 from the various tests. FIG. 5 shows three lines 46a, 46b, 46c of the acceleration a plotted against number of cycles (on a logarithmic scale) for three separate tests with identical test components 30. The elbow 48a, 48b, is shown for two of the lines 46a, 46b whilst the elbow for the third line 46c occurs at a greater number of cycles than is plotted. The fatigue limit 50 is a line fitted through all the elbows 48a, 48b and projected beyond these elbows. Thus the fatigue limit 50 is interpolated and extrapolated for other combinations of acceleration a and number of cycles than those tested.

As shown in FIG. 5 the fatigue limit 50 is a straight line against the logarithmic number of cycles. Alternatively the fatigue limit 50 may be non-linear. It is the best-fit line through the elbows 48a, 48b and may be described by a simple curve or a more complex equation. For example the best-fit line, fatigue limit 50, may be described by a quadratic, cubic or higher power expression; by a sinusoidal or exponential relationship; or by any other suitable relationship.

As is apparent from FIG. 5, the fatigue limit 50 is at a lower number of cycles for higher levels of acceleration a and is at a higher number of cycles for lower levels of acceleration a. Thus the fatigue limit 50 obeys an inverse relationship between the acceleration a and the number of cycles, which is linear against logarithmic cycles as illustrated.

The fatigue limit 50 may equally be plotted through the elbows 44a, 44b shown in FIG. 4. In this case the fatigue limit 50 is at a lower number of cycles for lower values of normalised phase and at a higher number of cycles for higher values of normalised phase, which represent smaller variation from the initial response phase φ. Thus the fatigue limit 50 obeys a positive relationship between the normalised phase and the number of cycles, and is linear against logarithmic cycles as illustrated.

Advantageously the change of response phase φ is much larger than the resultant change in resonant frequency $f_r$. For example, a phase change of 4% may result in a resonant frequency change of only 0.01% which is two orders of magnitude smaller. This is because the response phase φ amplifies structural changes for a structure with low damping.

Advantageously monitoring the first and/or second order derivative discontinuity of two or more parameters, whether input or output parameters, may provide information about the amount of energy dissipated by the test component 30 in the loading cycles before failure. The dissipated energy is the difference between the power input into the system, calculated for example from the force F and velocity v of the actuator 29, and the average power absorbed by the test component 30, calculated for example by the product of the mass m and acceleration a and velocity v of the test component 30. Instantaneous dissipated power may increase or decrease but over time the dissipated energy increases.

The output parameter measured by the output probe 34 or output probes 34 may additionally or alternatively be strain. It is noted that accurate measurement of strain is necessary in order that the discontinuity of the first and/or second order derivative is discernible. The measurement also needs to be continuous, or sampled at a high rate to seem continuous.

The temperature of the test component 30 may be iteratively measured. The temperature profile generated will exhibit a discontinuity after the critical number of cycles. Thus the temperature may be used instead of or in addition to any of the input and output parameters discussed above.

Although the response phase φ has been discussed as an output parameter, a different phase may be monitored. The response phase φ is between two outputs. Alternatively a phase between an input and an output of the system may be monitored for a discontinuity indicative of a critical event. For example, acoustic emissions may be monitored and the change of the response in terms of mode shape and/or nonlinearity may be monitored.

Composite materials are used for structural components in many engineering applications in which it is beneficial to characterise, and design around, fatigue limits 50. For example, composite materials may be used in the aerospace industry for aeroplane wings and bodies; gas turbine engine nacelles, fan blades, and rafts housing pipes and/or wires on the outside of the engine; and struts to connect the engine to the aircraft. Composite materials may also be used in transport industries: for automotive vehicles including to support and route cabling and pipework in the engine, and for lightweight bicycle frames. Composite materials may also be used in power plants, oil and gas pumping operations, marine applications, and for diesel engines.

The method is also suitable for obtaining the vibration fatigue limit 50 of materials other than composite materials. For example it can be used in vibration fatigue testing of metals and ceramics.

The steps of the method performed by the processor 36 may be encompassed in computer-implemented code and stored on a computer-readable medium. These steps are thus a computer-implemented method to determine a fatigue limit of a composite material. The method may be implemented on a basic computer system comprising a processing unit, memory, user interface means such as a keyboard and/or mouse, and display means. The method may be performed in 'real-time', that is at the same time that the data is measured in the vibration tests. Alternatively it may be performed 'offline' on data which has been measured and recorded previously, for example to obtain a more accurate fatigue limit 50 than was possible using previous methods.

Since composite materials fail progressively rather than abruptly, the fatigue limit 50 determined according to the present method is need not define the limit above which the composite material cannot be used. Instead it can be used as a warning that a finite amount of safe working life of the composite material remains. Thus the steps of the method can be used as a precursor to through-life monitoring of a component formed from composite material.

First the steps of the method are performed to identify the fatigue limit 50. Then the material can be periodically tested during life to determine where on the phase φ or acceleration a lines 42, 46 it is operating. A prediction can then be made as to how many cycles of material life remain for use of the component. The remaining material life may be determined by the probability of failure being below a threshold or by the material properties remaining above an acceptability threshold.

Figure 6:
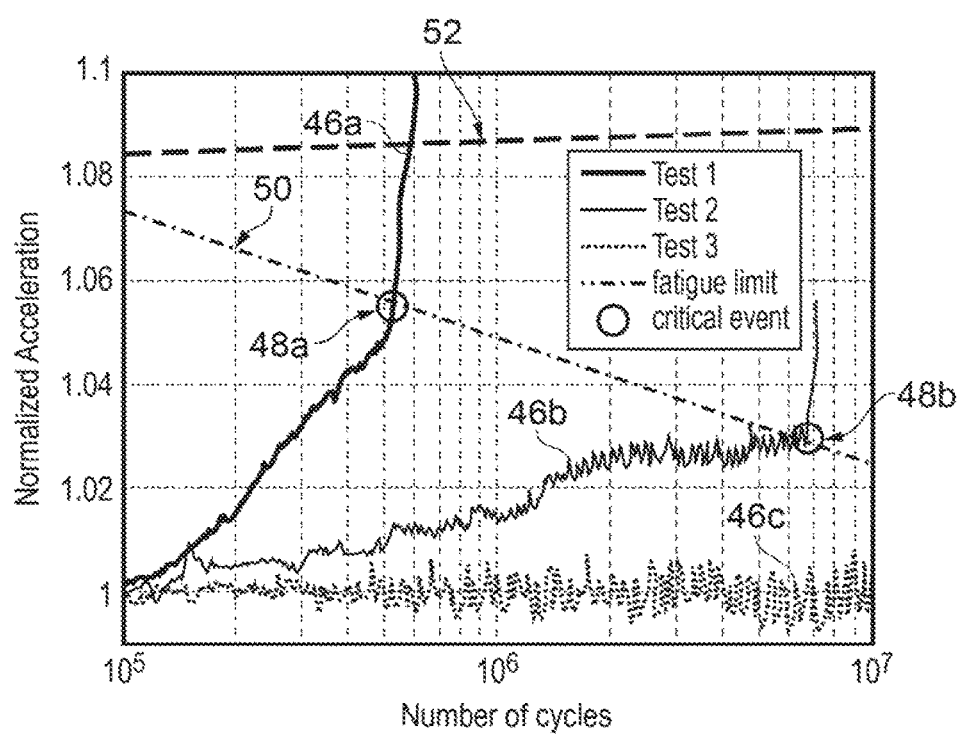
FIG. 6 is a graph showing normalised acceleration plotted against number of cycles and fatigue limit.

A failure limit 52 may be defined as the expected number of cycles at which the material will fail. The failure limit 52 may be defined according to a defined relationship to the vibration fatigue limit 50. An exemplary failure limit 52 is shown in FIG. 6, which is otherwise the same as FIG. 5. The failure limit 52 may be inversely related to the fatigue limit 50. So the material life between the fatigue limit 50 and the failure limit 52 is less where the material has been subject to aggressive cycles, line 46a, and is greater where the material has been subject to more benign cycles, lines 46b and 46c. The failure limit 52 may therefore be calculated by applying a multiplier to the fatigue limit 50.

The failure limit 52 is illustrated as linear against logarithmic cycles. Alternatively it may be described by a quadratic, cubic or higher power expression; by a sinusoidal or exponential relationship; or by any other suitable relationship. The failure limit 52 may be described by the same type of curve or equation as the fatigue limit 50. Alternatively it may be described by a different curve or equation.

It will be understood that the invention is not limited to the embodiments above-described and various modifications and improvements can be made without departing from the concepts described herein. Except where mutually exclusive, any of the features may be employed separately or in combination with any other features and the disclosure extends to and includes all combinations and sub-combinations of one or more features described herein.

The invention claimed is:

1. A method to determine a fatigue limit for a material comprising steps to:
   a. form a test component comprising the material;
   b. identify a resonant frequency of the test component;
   c. identify an excitation frequency which causes the test component to vibrate;
   d. measure the amplitude of vibration of the test component when excited at the excitation frequency;
   e. test the test component to determine its fatigue limit by sub-steps to:
      i. apply an excitation force to the test component at the excitation frequency to cause vibration of the test component;

ii. alter the applied excitation force at constant excitation frequency to maintain the amplitude of vibration constant;
iii. measure one or more input parameters, one or more output parameters, or a combination thereof;
iv. iterate steps ii and iii until the first order derivative, second order derivative, or first and second order derivatives of the input parameter, the output parameter, or the combination thereof exhibit a discontinuity;

f. repeat the steps a to e for a different excitation force; and g. define the fatigue limit for the material to include all the identified discontinuities.

2. A method as claimed in claim 1 wherein
in step 1.e.iii the input parameter comprises one or more of excitation force, acceleration, velocity, displacement, voltage and current, and determining input power therefrom.

3. A method as claimed in claim 1 wherein
in step 1.e.iii the output parameter comprises one or more of response phase, acceleration, velocity, displacement, voltage and current.

4. A method as claimed in claim 2 wherein
in step 1.e.iii the output parameter comprises one or more of response phase, acceleration, velocity, displacement, voltage and current.

5. A method as claimed in claim 1 wherein
the first order derivative, second order derivative, or first and second order derivatives is/are determined by plotting the input parameter, the output parameter, or the combination thereof against a number of vibration cycles; and identifying a point where the gradient of the plotted line changes.

6. A method as claimed in claim 5 wherein
the step of plotting comprises plotting logarithmically.

7. A method as claimed in claim 1 wherein
step 1.e comprises a high cycle fatigue test.

8. A method as claimed in claim 1 comprising a further step to determine a failure limit of the material.

9. A method as claimed in claim 8 wherein
the further step comprises applying a multiplier to the fatigue limit.

10. A method as claimed in claim 1 wherein
the material comprises a composite material.

* * * * *